(12) United States Patent
Akatsuka et al.

(10) Patent No.: US 6,812,318 B2
(45) Date of Patent: Nov. 2, 2004

(54) EPOXY RESINS, EPOXY RESIN MIXTURES, EPOXY RESIN COMPOSITIONS AND PRODUCTS OF CURING OF THE SAME

(75) Inventors: Yasumasa Akatsuka, Saitama (JP); Koji Nakayama, Saitama (JP); Katsuhiko Oshimi, Saitama (JP); Syouichi Tomida, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/149,164

(22) PCT Filed: Oct. 10, 2001

(86) PCT No.: PCT/JP01/08884
§ 371 (c)(1),
(2), (4) Date: Jul. 18, 2002

(87) PCT Pub. No.: WO02/31017
PCT Pub. Date: Apr. 18, 2002

(65) Prior Publication Data
US 2003/0065109 A1 Apr. 3, 2003

(30) Foreign Application Priority Data
Oct. 12, 2000 (JP) .................................. 2000-311558
Jan. 22, 2001 (JP) .................................. 2001-013164

(51) Int. Cl.⁷ .................................................. C08G 59/32
(52) U.S. Cl. ..................... 528/98; 528/103; 549/517; 549/545
(58) Field of Search .................... 549/517, 545; 523/466; 528/98, 103

(56) References Cited

U.S. PATENT DOCUMENTS 5,306,747 A    4/1994    Ito et al. .................... 523/433

FOREIGN PATENT DOCUMENTS

| EP | 0 013 532 | 7/1980 |
| JP | 51-143633 | 12/1976 |
| JP | 52083616 | * 7/1977 |
| JP | 61-47717 | 3/1986 |
| JP | 5-1265 | 1/1993 |
| JP | 11-255867 | 9/1999 |

OTHER PUBLICATIONS

Database Chemabs 'Online! Chemical Abstracts Service, Columbus, Ohio, US; Takagi, Yasuo et al: "2,6–and 3,5–Dihydroxytoluenediglycidyl ethers" XP002277850 retrieved from STN Database accession No. 87:184355 abstract* & 52 083616 A2 (Cemedine Co., Ltd., Japan; Mitsubishi Chemical Industries Co., Ltd.) Jul. 12, 1977 (Jul. 12, 1977).
Copy of the Supplementary European Search Report dated Apr. 23, 2004.

* cited by examiner

Primary Examiner—Philip Tucker
Assistant Examiner—D. Aylward
(74) Attorney, Agent, or Firm—Nields & Lemack

(57) ABSTRACT

The object of the present invention is to provide an epoxy resin and epoxy resin composition having a low viscosity which can afford a cured product having an excellent heat resistance. The present invention is characterized by using an epoxy resin which is obtained by reacting 5-methylresorcin with epihalohydrin in the presence of alkali metal hydroxide.

5 Claims, No Drawings

EPOXY RESINS, EPOXY RESIN MIXTURES, EPOXY RESIN COMPOSITIONS AND PRODUCTS OF CURING OF THE SAME

TECHNICAL FIELD

The present invention relates to low viscosity liquid epoxy resins or mixtures thereof and epoxy resin compositions which can afford a highly heat-resistant cured product. Epoxy resins and other matters of the present invention are useful for fabricating electric and electronic materials, laminating materials, coating compositions, adhesive compositions, and the like.

BACKGROUND IF THE INVENTION

Generally, epoxy resins can be hardened with the aid of various curing agents to form cured products which are excellent in mechanical properties, water resistance, chemical resistance, heat resistance, electrical properties, and the like. Hence, they are widely used in various fields such as adhesive compositions, coating compositions, laminated boards, molding materials, casting materials and the like. Among liquid epoxy resins that have been most commonly used in industrial applications, well-known is a compound obtained by reacting epichlorohydrin with bisphenol A. Cresol novolak type epoxy resins have been widely used as a sealing medium for semiconductor devices, since such a sealing medium requires a good heat resistance. It has also been proposed recently to apply liquid epoxy resin compositions to semiconductor mounting methods.

However, such an epoxy resin composition to be used in semiconductor mounting methods is required to have a high glass transition point so as to prevent the substrate from warping due to the shrinkage of the composition on curing. Another requirement is that these compositions should have a low viscosity to allow the resin to penetrate into all details of semiconductor junctions. However, the existing bisphenol A type epoxy resins, which have been commonly used, have a viscosity as high as about 10 Pa·s at 25° C. and a glass transition point of the order of 160° C. even when cured with the aid of acid anhydride, and therefore cannot satisfy the properties required for the said application.

SUMMARY OF THE INVENTION

In view of the actual circumstances as stated above, the present inventors have made much effort in searching for a liquid epoxy resin having both an excellent heat resistance and a low viscosity. Our efforts have allowed us to find that an epoxy resin having a specific molecular structure has a low viscosity and exhibits an excellent heat resistance when cured. These findings have led us to achieve the present invention.

That is, the present invention provides:

(1) an epoxy resin represented by the formula (1):

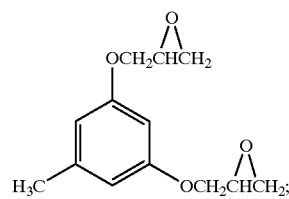

(2) an epoxy resin mixture obtained by mixing an epoxy resin of the above formula (1) with an epoxy resin represented by the following formula (2):

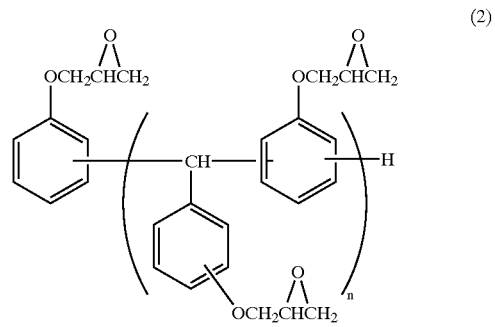

in which, n is an integer indicating the number of repeating unit;

(3) the epoxy resin mixture as defined in the item (2), wherein the mixture is obtained by mixing 10 to 90 parts by weight of an epoxy resin of the formula (1) with 90 to 10 parts by weight of an epoxy resin of the formula (2);

(4) an epoxy resin composition comprising an epoxy resin as defined in the item (1) and a curing agent;

(5) the epoxy resin composition as defined in the item (4), wherein the composition further contains a curing accelerator;

(6) the epoxy resin composition as defined in the item (4) or (5), wherein the composition further contains an inorganic filler;

(7) the epoxy resin composition as defined in anyone of the items (4) to (6), wherein the composition comprises as an epoxy resin component an epoxy resin mixture as defined in the item (2) or (3);

(8) a cured product obtained by hardening an epoxy resin composition as defined in anyone of the items (4) to (6); and, (9) a cured product obtained by hardening an epoxy resin composition as defined in the item (7).

The present invention will now be described in more details. In the following descriptions, "part" and "%" are always on the weight basis.

An epoxy resin of the formula (1) as defined above in the item (1) can be obtained, for example, by reacting a compound of the formula (a):

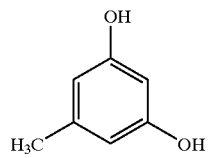

(a)

with epihalohydrin in the presence of an alkali metal hydroxide.

In the reaction for producing the epoxy resin of the present invention, alkali metal hydroxide may be used in the form of aqueous solution. In that case, the process may be designed in such a way that while continuously introducing the aqueous solution of alkali metal hydroxide into the reaction system, water and epihalohydrin are continuously discharged under reduced or normal pressure. And then, the epihalohydrin is separated from the water, the latter being removed and the former being continuously recycled to the reaction system.

Alternatively, the process may be a process comprising adding a quaternary ammonium salt as a catalyst such as tetramethylammonium chloride, tetramethylammonium bromide or trimethylbenzylammonium chloride to a mixture of a compound of the formula (a) with epihalohydrin; reacting the resulting mixture at a temperature of 50 to 150° C. for 0.5 to 8 hours to form a halohydrin etherified product of the compound of the formula (a); and then dehydrohalogenating (ring-closing) the halohydrin etherified product by adding alkali metal hydroxide in the form of solid or aqueous solution and reacting the resulting mixture at a temperature of 20 to 120° C. for 1 to 10 hours.

The amount of epihalohydrin to be usually used in these reactions is generally 0.8 to 12 mol, preferably 0.9 to 11 mol, for one equivalent of the hydroxyl group in the compound of the formula (a). In order to make the reaction proceed smoothly, the reaction is preferably carried out with the addition of an alcohol such as methanol or ethanol or an aprotic polar solvent such as dimethylsulfone or dimethyl sulfoxide.

When an alcohol is used, the amount of the alcohol to be used is usually 2 to 20%, preferably 4 to 15% on the basis of the amount of epihalohydrin. Alternatively, when a aprotic polar solvent is used, the amount of the solvent to be used is usually 5 to 150%, preferably 10 to 140% on the basis of the amount of epihalohydrin.

After optionally washed with water, the reaction products thus obtained from such epoxidation reactions are heated under reduced pressure to remove epihalohydrin, solvents and the like. Additionally, in order to obtain an epoxy resin with poorer hydrolyzable halogen, the ring closure may be ensured by dissolving the collected epoxy resin in a solvent such as toluene or methyl isobutyl ketone; adding an aqueous solution of alkali metal hydroxide such as sodium hydroxide or potassium hydroxide; and then reacting the resulting mixture. In this case, the alkali metal hydroxide is usually used in an amount of 0.01 to 0.3 mol, preferably 0.05 to 0.2 mol for one equivalent of the hydroxyl group in the compound of the formula (a) to be epoxidized. The reaction temperature is usually 50 to 120° C. and the reaction time is usually 0.5 to 2 hours.

After the reaction is completed, the resulting salt is removed by filtration, water washing or the like, and the solvent is then distilled off by heating under reduced pressure to give an epoxy resin of the present invention.

The epoxy resins of the present invention obtained as set forth above, which are liquid at normal temperature and are excellent in workability, may be used in combination with epoxy resins which are semi-solid at normal temperature or have a softening point of 50 to 80° C. such as epoxy resins represented by the following formula (2) to afford an epoxy resin component (epoxy resin mixture of the present invention) that is liquid at normal temperature without causing any damage to their physical properties, hence resulting in a favorable effect.

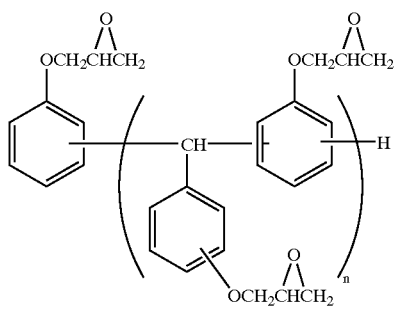

(2)

in which n is an integer indicating the number of repeating unit and usually denotes 1 to 5, preferably 1 to 3, in average.

No special limitations are imposed on epoxy resins of the formula (2), if only they are a triphenyl-methane type epoxy resin represented by the formula (2). Illustrative examples thereof include EPPN-501 H (mfd. by Nippon Kayaku Co.), EPPN-501 HY (mfd. by Nippon Kayaku Co.) and EPPN-502 H (mfd. by Nippon Kayaku Co.). EPPN-501 H, which is semi-solid and has a low melting viscosity, is particularly preferred.

The mixing ratio of the epoxy resin of the formula (1) to the epoxy resin of the formula (2) is usually in the range of from 10:90 to 90:10 on the weight basis, preferably 20:80 to 80:20, more preferably 30:70 to 70:30.

No special limitations are imposed on the method for mixing them as long as it can provide their homogeneous mixture. An epoxy resin composition of the present invention may be obtained by adding epoxy resins of the formulae (1) and (2) without previously mixing them, as set forth below.

Epoxy resin compositions of the present invention will be explained below.

In an epoxy resin composition of the present invention, an epoxy resin or epoxy resin mixture of the present invention can be used alone or in combination with other epoxy resins. In the combined use, the epoxy resin or epoxy resin mixture of the present invention is preferably present at a proportion of 30% or more, particularly 40% or more of the whole epoxy resins.

Specific examples of the other epoxy resin which may be used in combination with the epoxy resin of the present invention include, but are not limited to, novolak type epoxy resins, condensed dicyclopentadiene phenol type epoxy resins, xylylene skeleton-containing phenolic novolak type epoxy resins, biphenyl skeleton-containing novolak type epoxy resins, bisphenol A type epoxy resins, bisphenol F type epoxy resins, and tetramethylbiphenol type epoxy resins. These epoxy resins may be used alone or in combination of 2 or more.

The curing agent to be contained in the epoxy resin composition of the present invention may be an amine, acid anhydride, amide, or phenol compound. Specific examples of the curing agent which can be used include, but are not limited to, diaminodiphenylmethane, diethylenetriamine, triethylenetetramine, diaminodiphenylsulfone, isophoronediamine, dicyandiamide, polyamide resins synthesized from linolenic acid dimer and ethylenediamine, phthalic anhydride, trimellitic anhydride, pyromellitic anhydride, maleic anhydride, tetrahydrophthalic anhydride, methyltetrahydrophthalic anhydride, methylnadic anhydride, hexahydrophthalic anhydride, methylhexahydrophthalic anhydride, phenolic novolak, and modifications thereof, imidazole, $BF_3$-amine complex, and guanidine derivatives. These curing agents may be used alone or in combination of 2 or more.

The amount of the curing agent to be used in the epoxy resin composition of the present invention is preferably 0.7 to 1.2 equivalent for one equivalent of the epoxy resin. When the curing agent is used at an amount of less than 0.7 equivalent or more than 1.2 equivalent for one equivalent of the epoxy group, the composition may fail to attain the complete curing and to exhibit good physical properties after cured.

A curing accelerator can also be incorporated without any inconvenience into the epoxy resin composition of the present invention. Specific examples of the curing accelerator which can be used include imidazoles such as 2-methylimidazole, 2-ethylimidazole and 2-ethyl-4-methylimidazole; tertiary amines such as 2-(dimethylaminomethyl)phenol and 1,8-diaza-bicyclo(5.4.0)-undecene-7; phosphines such as triphenylphosphine; and metallic compounds such as tin octylate. The curing accelerator is optionally used in an amount of 0.1 to 5.0 parts for 100 parts of the epoxy resin.

Inorganic fillers may be optionally incorporated into the epoxy resin composition of the present invention. Specific examples of the inorganic filler which can be used include silica, alumina, and talc. The inorganic filler is used in the epoxy resin composition of the present invention at a proportion of 0 to 90%. In addition, the epoxy resin composition of the present invention may contain various compounding additives including silane coupling agents, releasing agents such as stearic acid, palmitic acid, zinc stearate, and calcium stearate, and pigments.

Epoxy resin compositions of the present invention can be obtained through the intimate mixing of the ingredients. An epoxy resin composition of the present invention can be easily turned into a cured product by a method similar to conventional methods. For example, a cured product may be obtained by blending and sufficiently homogenizing epoxy resin components, curing agents and optional ingredients such as curing accelerators, inorganic fillers and compounding additives optionally by means of extruder, kneader, roll or the like to obtain an epoxy resin composition; melting the epoxy resin composition; molding the melted epoxy resin composition in a casting or transfer molding machine; and then heating the molded product at a temperature of usually 80 to 200° C. for 2 to 10 hours.

Alternatively, a cured product may be also obtained by dissolving an epoxy resin composition of the present invention in a solvent such as toluene, xylene, acetone, methyl ethyl ketone, or methyl isobutyl ketone to obtain a solution of the epoxy resin composition; impregnating a base material made of glass fiber, carbon fiber, polyester fiber, polyamide fiber, alumina fiber, paper or the like with the solution; heating the thus impregnated base material to semi-dried state to give a prepreg; and then hot press molding the prepreg. Here, the solvent is used in an amount of usually 10 to 70%, preferably 15 to 70% of the mixture of the epoxy resin composition of the present invention and the solvent.

EXAMPLES

The present invention will now be described more definitely by way of examples.

Example A1

Into a flask equipped with a thermometer, a dropping funnel, a cooling tube and a stirrer and placed under purging with nitrogen gas, were charged 62 parts of a compound of the formula (a), 370 parts of epichlorohydrin and 92.5 parts of dimethyl sulfoxide. The resulting mixture was dissolved by heating it to 45° C. with stirring. Then, 40.4 parts of flaky sodium hydroxide was added portionwise over 100 minutes. The resulting mixture was allowed to react at 45° C. for additional 3 hours and at 70° C. for 1 hour. Upon completion of the reaction, dimethyl sulfoxide and excess epichlorohydrin were distilled off by using rotary evaporator with heating under reduced pressure. The residue was dissolved in 236 parts of methyl isobutyl ketone.

The thus obtained methyl isobutyl ketone solution was heated to 70° C. and 10 parts of an aqueous 30% sodium hydroxide solution was added. The resulting mixture was allowed to react for 1 hour and was then repeatedly washed with water until washing liquors became neutral. Thereafter, the aqueous layer was separated and removed to obtain 114 parts of the epoxy resin (A) of the present invention represented by the above formula (1). The obtained epoxy resin was liquid and had a viscosity of 0.60 Pa·s at 25° C. as measured by means of E type viscometer and an epoxy equivalent of 131 g/eq.

Example A2

To the epoxy resin (A) obtained in Example A1, Kayahard MCD (methylnadic anhydride; mfd. by Nippon Kayaku Co.) as a curing agent and triphenylphosphine (TPP) as a curing accelerator were blended in the weight ratio indicated in the column labeled "composition of blend" in the table 1. The resulting blend was intimately mixed and then cast into a mold. The thus molded blend was allowed to cure at 80° C. for 2 hours, at 120° C. for 2 hours and at 180° C. for 4 hours to prepare a specimen. Glass transition temperature of the specimen measured under the following conditions is shown in the column labeled "physical properties of hardened product" in the table 1.

Glass Transition Point

Thermomechanical measuring apparatus (TMA): Shinku Riko (Inc.) TM-7000

Heat-up rate: 2° C./min.

TABLE 1

|  | Example A2 |
|---|---|
| Composition of blend | |
| epoxy resin (A) | 100 |
| Kayahard MCD | 120 |
| TPP | 1 |
| Physical properties of hardened product | |
| glass transition point (° C.) | 175 |

Example B1

EPPN-501 H (epoxy equivalent 165 g/eq, semi-solid at 25° C.; mfd. by Nippon Kayaku Co.) as a triphenylmethane type epoxy resin represented by the above formula (2) was intimately mixed with the epoxy resin (A) prepared in Example A1 in the weight ratio of 50:50 to obtain an epoxy resin mixture (B) of the present invention. The obtained epoxy resin mixture (B) had an epoxy equivalent of 146 g/eq and a viscosity of 13.0 Pa·s at 25° C. as measured by means of E type viscometer.

Example B2

To the epoxy resin mixture (B) prepared in Example B1, Kayahard MCD (methylnadic anhydride; mfd. by Nippon Kayaku Co.) as a curing agent and 2-ethyl-4-methylimidazole (2E4MZ) as a curing accelerator were blended in the weight ratio indicated in the column labeled "composition of blend" in the table 2. The resulting blend was intimately mixed and then cast into a mold. The thus molded blend was allowed to cure at 80° C. for 2 hours, at 120° C. for 2 hours and at 180° C. for 4 hours to prepare a specimen. Glass transition temperature of the specimen measured under the above conditions is shown in the column labeled "physical properties of hardened product" in the table 2.

TABLE 2

|  | Example B2 |
|---|---|
| Composition of blend | |
| epoxy resin (B) | 100 |
| Kayahard MCD | 108 |
| 2E4MZ | 1 |
| Physical properties of hardened product | |
| glass transition point (° C.) | 185 |

As seen from Tables 1 and 2, the cured products obtained by hardening the epoxy resin compositions comprising the epoxy resin or epoxy resin mixture of the present invention exhibited a very excellent heat resistance (as judged from a high glass transition point).

Test Example

The epoxy resin (A) obtained in Example A1 was subjected to Ames test using 5 strains designated by GLP (Good Laboratory Practice) at the institution (BML Inc.) that satisfied the legal requirements prescribed in the Industrial Safety and Health Law and in the Law Concerning Examination and Regulation of Manufacture and Handling of Chemical Substances. The test result was negative for every strain of every preset concentration.

Effects of the Invention

As is evident from the negative results in Ames test, epoxy resins of the present invention are low-toxic, hence can bring a remarkable improvement on working environment.

Moreover, epoxy resin compositions containing an epoxy resin or epoxy resin mixture of the present invention can provide a cured product which is excellent in heat resistance and water resistance as compared with conventional epoxy resin compositions which have been commonly used.

Therefore, epoxy resin compositions of the present invention are very useful for a wide variety of applications including electric and electronic materials, molding materials, casting materials, laminating materials, coating compositions, adhesive compositions, resists, and optical materials.

What is claimed is:

1. An epoxy resin mixture obtained by mixing an epoxy resin represented by the following formula (1):

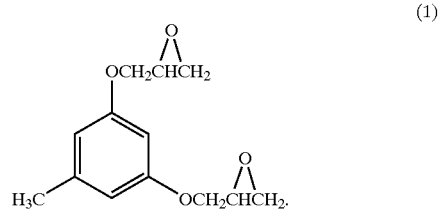

with an epoxy resin represented by the following formula (2):

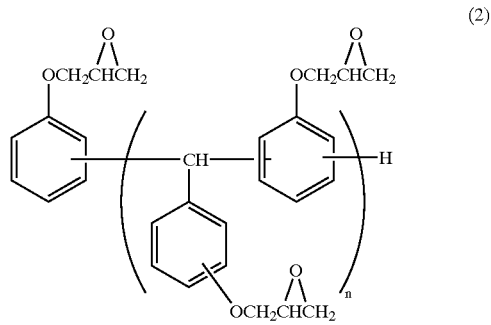

in which, n is an integer indicating the number of repeating units.

2. The epoxy resin mixture according to claim 1, wherein the mixture is obtained by mixing 10 to 90 parts by weight of an epoxy resin of the formula (1) with 90 to 10 parts by weight of an epoxy resin of the formula (2).

3. An epoxy resin composition comprising an epoxy resin mixture of claim 1 or 2 and a curing agent.

4. The epoxy resin composition according to claim 3, wherein the composition further contains a curing accelerator.

5. A cured product obtained by hardening an epoxy resin composition of claim 3.

* * * * *